United States Patent [19]

Jeanson et al.

[11] Patent Number: 5,723,013
[45] Date of Patent: Mar. 3, 1998

[54] SPACER IMPLANT FOR SUBSTITUTING MISSING VERTEBRAE

[75] Inventors: Jean-Francois Jeanson, Assenay; Marc Ameil, Reims; Hervé Dinville, Saint-Parres-Aux-Tertres; Jean Huppert, L'Étrat; Thierry Marnay, Nimes; Michel Gau, St. Pol Sur Ternoise, all of France

[73] Assignee: JBS S.A., Troyes, France

[21] Appl. No.: 595,955

[22] Filed: Feb. 6, 1996

[30] Foreign Application Priority Data

Feb. 6, 1995 [FR] France .................. 95 01326

[51] Int. Cl.$^6$ ............................................. A61F 2/44
[52] U.S. Cl. ............................. 623/17; 606/61; 606/73
[58] Field of Search .......................... 623/16, 17, 18; 606/61, 73, 74, 75

[56] References Cited

U.S. PATENT DOCUMENTS

| | | | |
|---|---|---|---|
| 4,157,715 | 6/1979 | Westerhoff | 606/60 |
| 4,567,884 | 2/1986 | Edwards | 606/61 |
| 4,657,550 | 4/1987 | Daher | 606/61 |
| 4,870,957 | 10/1989 | Goble et al. | 606/73 |
| 4,892,545 | 1/1990 | Day et al. | 606/61 |
| 5,290,312 | 3/1994 | Kojimoto et al. | 623/17 |

FOREIGN PATENT DOCUMENTS 9503745  2/1995  WIPO ................................ 606/73

Primary Examiner—David Isabella
Attorney, Agent, or Firm—Spencer & Frank

[57] ABSTRACT

An implant for replacing a removed vertebra includes an outer sleeve having a longitudinal axis and a peripheral inner surface. The inner surface has a series of axially adjoining, peripheral grooves lending the inner surface a sawtooth-shaped configuration when viewing the inner sleeve in axial section. The implant further includes an inner sleeve having a longitudinal axis and a peripheral outer surface. The outer surface has a series of axially adjoining, peripheral ribs lending the outer surface a sawtooth-shaped configuration when viewing the inner sleeve in axial section. The inner sleeve is telescopingly received in the outer sleeve such that the series of axially adjoining, peripheral ribs of the outer surface engage into the series of axially adjoining, peripheral grooves of the surface in an interfitting relationship. The sawtooth-shaped configurations of the inner and outer surfaces are oriented such that in normal operation the sleeves are prevented by the interengaging sawtooth configurations from being telescoped into one another, but are allowed by ratchet action to telescope outwardly from one another. The inner sleeve is radially sufficiently resilient to allow alternating radial compression and expansion during the ratchet action.

6 Claims, 1 Drawing Sheet

SPACER IMPLANT FOR SUBSTITUTING MISSING VERTEBRAE

BACKGROUND OF THE INVENTION

This invention relates to a spacer implant for substituting missing vertebrae and has elements that are axially adjustable.

When damage occurs along the spinal column to the vertebrae or a tumor is removed, it is common practice to use an autolog bone (graft) from the bone structure, or to perform an alloplastic operation and/or to apply a mechanical spacer for the implantation.

The spinal area must be supported and stabilized even if using autolog or alloplastic techniques as an autolog graft requires great lengths of time to embed, so immediate stress and pressure to the vertebrae cannot be applied. Thus recovery requires a considerable length of time.

In such cases titanium-mesh cylinders are commonly used which surround the material implanted in the area affected by the vertebrectomy and which can mechanically support the neighboring vertebrae. These titanium-mesh cylinders must be used with bone screws and stabilizing rods, thus making their use complicated and time-consuming.

Another common method is to bridge the gap, from a vertebrectomy, with a spacer which can be varied in length and which is attached to the bone with a series of claws. The spacer's length has to be adjusted with fixing screws on both sides of the apparatus, thus making its use difficult during surgery.

SUMMARY OF THE INVENTION

It is an object of the invention to provide an improved implant which has a very simple construction for substituting missing vertebrae and which can be quickly, simply and safely implanted.

This object and others to become apparent as the specification progresses, are accomplished by the invention, according to which, briefly stated, the implant for replacing a removed vertebra includes an outer sleeve having a longitudinal axis and a circumferential inner surface. The inner surface has a series of axially adjoining, circumferential grooves lending the inner surface a sawtooth-shaped configuration when viewing the inner sleeve in axial section. The implant further includes an inner sleeve having a longitudinal axis and a circumferential outer surface. The outer surface has a series of axially adjoining, circumferential ribs lending the outer surface a sawtooth-shaped configuration when viewing the inner sleeve in axial section. The inner sleeve is telescopingly received in the outer sleeve such that the series of axially adjoining, circumferential ribs of the outer surface engage into the series of axially adjoining, circumferential grooves of said the surface in an interfitting relationship. The sawtooth-shaped configurations of the inner and outer surfaces are oriented such that in normal operation the sleeves are prevented by the interengaging sawtooth configurations from being telescoped into one another, but are allowed by ratchet action to telescope outwardly from one another. The inner sleeve is radially sufficiently resilient to allow alternating radial compression and expansion during the ratchet action.

According to a preferred embodiment, the elements are hollow bodies and the inner surface of the outer element has sawtooth shaped ring-grooves so that the thin walled inner element can be connected to the outer element by way of sawtooth shaped ribs arranged at least at the end of the element. The grooves and ribs allow distraction while hindering compression.

Preferably, at least two axial slots are provided in the wall of the inner element, running from the end provided with ribs and the outer element is provided with grooves cooperating with the slots.

The hollow elements may have open ends closed with a plug provided with axial claws or a base plate may be inserted in one of the open ends.

According to another embodiment, one end of the hollow elements may be open and the other end is provided with a base plate having axial claws.

DESCRIPTION OF THE PREFERRED EMBODIMENT

Figure 1:
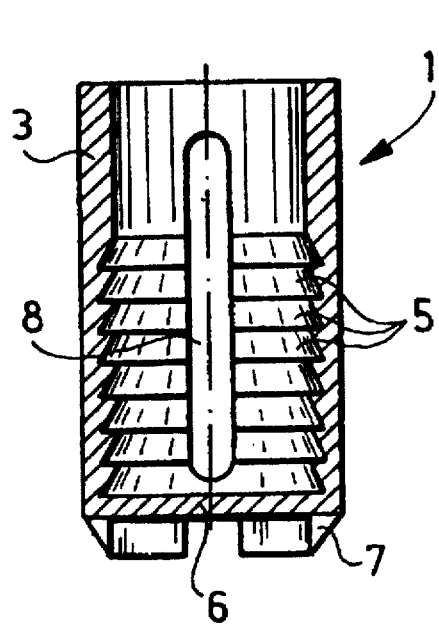
FIG. 1 is an axial sectional view of an outer element of the implant according to the invention.
Figure 2:
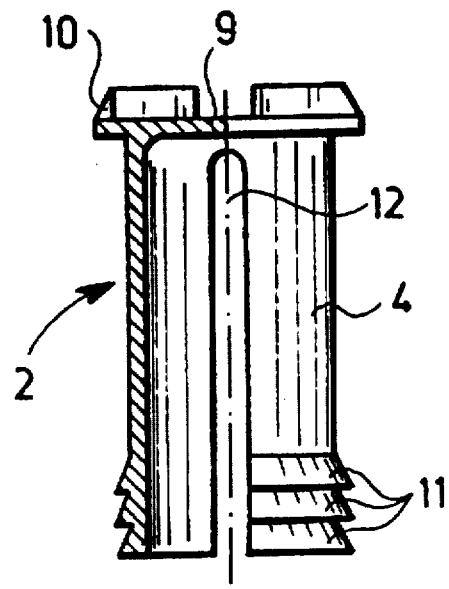
FIG. 2 is an axial sectional view of an inner element of the implant.
Figure 3:
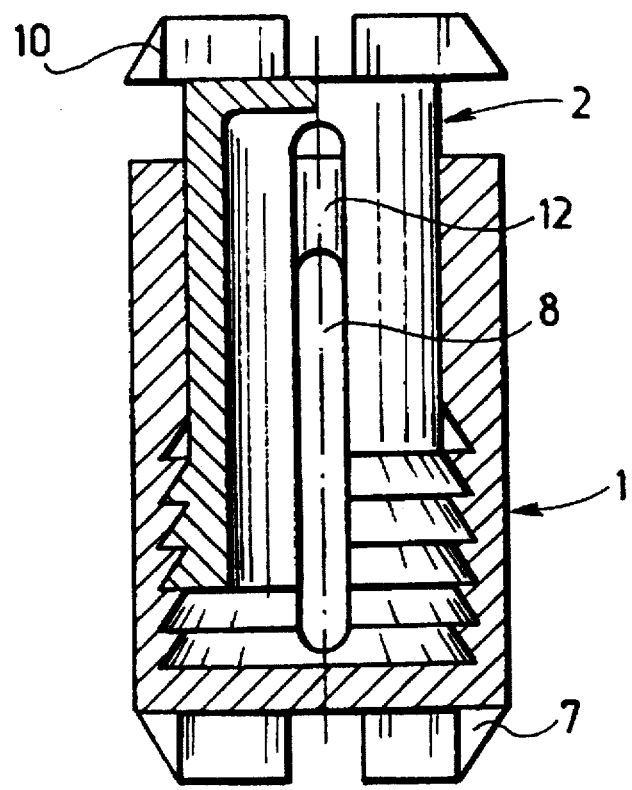
FIG. 3 is an axial sectional view of the assembled implant.

The implant shown in FIGS. 1 to 3 is composed of an outer element 1 having a cylindrical body 3 and an inner element 2 having a cylindrical body 4.

Turning to FIG. 1, the outer surface of body 3 is smooth, while its inner surface contains ring-shaped grooves 5 having a sawtooth shaped cross section. At the lower end of body 3 a base plate 6 is provided, having claws 7. In the wall of body 3, two axially extending, facing slots 8 are provided.

Turning to FIG. 2, the body 4 of the inner element 2 is provided with a base plate 9 having claws 10 on its outer surface. The outer cylindrical surface of element 2 is provided with ribs 11 in the bottom region, remote from the base plate 9. The ribs 11 are also sawtooth shaped and can be received by the ring shaped grooves 5 of element 1. The body 4 is thinner-walled than the body 3 and is provided with axial slots 12 almost on its entire length. Slots 12 and the thin wall of the body 4 lend the element 2 a resilient structure and, accordingly, inner element 2 may be inserted into outer element 1 as shown in FIG. 3. Due to the orientation of the sawtooth shaped grooves 5 and ribs 11 and the resilient structure, the inner element 2 may be moved outwardly from the outer element 1, while the ribs 11 of the inner element 2 resiliently ride on slots 5 of the outer element 1 in a ratchet-like manner. In this way, the inner and outer elements 1, 2 of the spacer implant are stabilized against compression in every possible arrangement, while permitting decompressive movements.

If the slots 8 of the outer element 1 and the grooves 12 of the inner element 2 are aligned, wedges may be placed thereinto to fix the position of the elements 1, 2 relative to one another.

Thus, the implantation can be achieved by compressing the apparatus entirely and placing it into the affected area of the vertebrectomy, so that the apparatus fits in-between the nearest vertebrae. Using a pair of pliers, the elements 1 and 2 are pushed apart until the neighboring vertebrae are in proper position.

This way, the implantation only requires two simple steps, which can be completed with great safety and ease during surgery. If needed, the elements can be wedged as explained earlier.

The method made possible by this implant simplifies the process of implanting bone grafts, compared to the techniques used to date, because the adjustable elements do not require a separate manipulation for stabilization, since once the desired length of the apparatus is set it can not slip or readjust by a bad movement.

It is to be understood that, instead of claws, the implant may have other supportive elements, such as supportive plates. The bodies 3 and 4 may be open at both ends, thus making it possible to insert into one end a plug provided with a supportive plate or claws. The elements can also have shapes other than cylindrical; they may be, for example, rectangular.

It will be understood that the above description of the present invention is susceptible to various modifications, changes and adaptations, and the same are intended to be comprehended within the meaning and range of equivalents of the appended claims.

We claim:

1. An implant for replacing a removed vertebra, comprising
   (a) an outer sleeve having a longitudinal axis and an inner surface having a periphery; said inner surface having a series of axially adjoining grooves each extending along a substantial part of said periphery; the groove series lending said inner surface a sawtooth-shaped configuration when viewing said outer sleeve in axial section; and
   (b) an inner sleeve having a longitudinal axis and an outer surface having a periphery; said outer surface having a series of axially adjoining ribs each extending along a substantial part of said periphery of said outer surface; the rib series lending said outer surface a sawtooth-shaped configuration when viewing said inner sleeve in axial section; said inner sleeve being telescopingly received in said outer sleeve such that said series of ribs of said outer surface engage into said series of grooves of said inner surface in an interfitting relationship; said sawtooth-shaped configurations of said inner and outer surfaces being oriented such that in normal operation said sleeves are prevented by the interengaging sawtooth configurations from being telescoped into one another and are allowed by ratchet action to telescope outwardly from one another; said inner sleeve being radially sufficiently resilient to allow alternating radial compression and expansion of said inner sleeve during the ratchet action.

2. The implant as defined in claim 1, wherein said inner and outer sleeves are cylindrical and said grooves and ribs are ring-shaped.

3. The implant as defined in claim 1, further comprising axial slots provided in said inner and outer sleeves.

4. The implant as defined in claim 1, wherein said inner sleeve has opposite axial ends and said series of ribs extends from one of said ends; further comprising an axial slot extending in said inner sleeve from said one end.

5. The implant as defined in claim 1, wherein said inner and outer sleeves each have an open end and a closed end; said open end of said inner sleeve being situated inside said outer sleeve and facing the closed end of said outer sleeve; said closed end of said inner sleeve being situated externally of said outer sleeve.

6. The implant as defined in claim 5, said closed ends of said inner and outer sleeves carrying outwardly and axially oriented claws.

* * * * *